United States Patent
Lim et al.

(10) Patent No.: US 11,930,858 B2
(45) Date of Patent: Mar. 19, 2024

(54) AEROSOL GENERATING DEVICE AND METHOD FOR SHOWING THE REMAINING AMOUNT OF LIQUID COMPOSITION USING LIGHT SOURCE

(71) Applicant: KT&G CORPORATION, Daejeon (KR)

(72) Inventors: Hun Il Lim, Seoul (KR); Tae Hun Kim, Yongin-si (KR); Hyung Jin Jung, Seoul (KR); Jae Sung Choi, Seoul (KR); Jung Ho Han, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 579 days.

(21) Appl. No.: 17/276,545

(22) PCT Filed: Oct. 6, 2020

(86) PCT No.: PCT/KR2020/013574
§ 371 (c)(1),
(2) Date: Mar. 16, 2021

(87) PCT Pub. No.: WO2021/071203
PCT Pub. Date: Apr. 15, 2021

(65) Prior Publication Data
US 2022/0295904 A1    Sep. 22, 2022

(30) Foreign Application Priority Data
Oct. 11, 2019   (KR) .................... 10-2019-0126291

(51) Int. Cl.
*A24F 40/10*   (2020.01)
*A24F 7/00*   (2006.01)
(Continued)

(52) U.S. Cl.
CPC ................ *A24F 40/60* (2020.01); *A24F 7/00* (2013.01); *A24F 40/10* (2020.01); *A24F 40/20* (2020.01);
(Continued)

(58) Field of Classification Search
None
See application file for complete search history.

(56) References Cited

U.S. PATENT DOCUMENTS 10,092,036 B2   10/2018  Phillips et al.
10,779,572 B2    9/2020  Mironov et al.
(Continued)

FOREIGN PATENT DOCUMENTS

CN   204377922 U   6/2015
CN   107951077 A   4/2018
(Continued)

OTHER PUBLICATIONS

Office Action dated Apr. 20, 2023 in Chinese Application No. 202080006051.9.
(Continued)

*Primary Examiner* — Ross N Gushi
(74) *Attorney, Agent, or Firm* — Sughrue Mion, PLLC

(57) ABSTRACT

An aerosol generating device according to an aspect comprises a main body that comprises a battery and a controller, a cartridge which is coupled to the main body and comprises a liquid storage that contains liquid composition and an atomization portion that generates an aerosol by heating the liquid composition contained in the liquid storage, and a cover that forms an inner space by being coupled to the main body such that the cartridge is arranged in the inner space, wherein the main body further comprises a light source that emits light toward an inside of the liquid storage, and the cover comprises a window hole through which light entitled
(Continued)

from the light source toward the inside of the liquid storage is transmitted to the outside of the cover.

15 Claims, 9 Drawing Sheets

(51) Int. Cl.
| | |
|---|---|
| *A24F 40/20* | (2020.01) |
| *A24F 40/30* | (2020.01) |
| *A24F 40/42* | (2020.01) |
| *A24F 40/51* | (2020.01) |
| *A24F 40/60* | (2020.01) |
| *G01F 23/80* | (2022.01) |

(52) U.S. Cl.
CPC .............. *A24F 40/30* (2020.01); *A24F 40/42* (2020.01); *A24F 40/51* (2020.01); *G01F 23/80* (2022.01)

(56) References Cited

U.S. PATENT DOCUMENTS

| | | | |
|---|---|---|---|
| 10,881,131 B2 | 1/2021 | Matsumoto et al. | |
| 11,311,688 B2* | 4/2022 | Phillips | A24F 40/70 |
| 11,588,287 B2* | 2/2023 | Novak, III | H05B 3/22 |
| 11,690,963 B2* | 7/2023 | Danek | A61M 15/0085 |
| | | | 131/328 |
| 11,758,948 B2* | 9/2023 | Ricketts | A24F 40/42 |
| | | | 131/273 |
| 2017/0245553 A1 | 8/2017 | Reevell | |
| 2017/0258138 A1 | 9/2017 | Rostami et al. | |
| 2018/0360125 A1 | 12/2018 | James et al. | |
| 2019/0191783 A1 | 6/2019 | Courbat et al. | |
| 2019/0231997 A1 | 8/2019 | Ricketts et al. | |
| 2019/0289914 A1 | 9/2019 | Liu et al. | |
| 2020/0323264 A1 | 10/2020 | Kim et al. | |
| 2023/0014895 A1* | 1/2023 | Novak, III | A24F 40/90 |

FOREIGN PATENT DOCUMENTS

| | | |
|---|---|---|
| EP | 0 845 220 B1 | 9/2003 |
| JP | 2018-514200 A | 6/2018 |
| JP | 2019-503677 A | 2/2019 |
| JP | 2019-506894 A | 3/2019 |
| JP | 2019-521671 A | 8/2019 |
| KR | 10-1550330 B1 | 9/2015 |
| KR | 10-1820847 B1 | 1/2018 |
| KR | 10-2019-0049397 A | 5/2019 |
| KR | 10-2000853 B1 | 7/2019 |
| WO | 2018/069849 A1 | 4/2018 |
| WO | 2019/088580 A2 | 5/2019 |
| WO | 2019/145104 A1 | 8/2019 |

OTHER PUBLICATIONS

Korean Office Action for 10-2019-0126291 dated Jan. 27, 2021.
International Search Report for PCT/KR2020/013574 dated, Jan. 13, 2021 (PCT/ISA/210).
Written Opinion of the International Searching Authority for PCT/KR2020/013574 dated Jan. 13, 2021 (PCT/ISA/237).
Notice of Reasons for Refusal dated Aug. 2, 2022 from the Japanese Patent Office in Japanese Application No. 2021-531435.
Extended European Search Report dated Nov. 19, 2021 in European Application No. 20859673.4.

* cited by examiner

[Fig. 1]
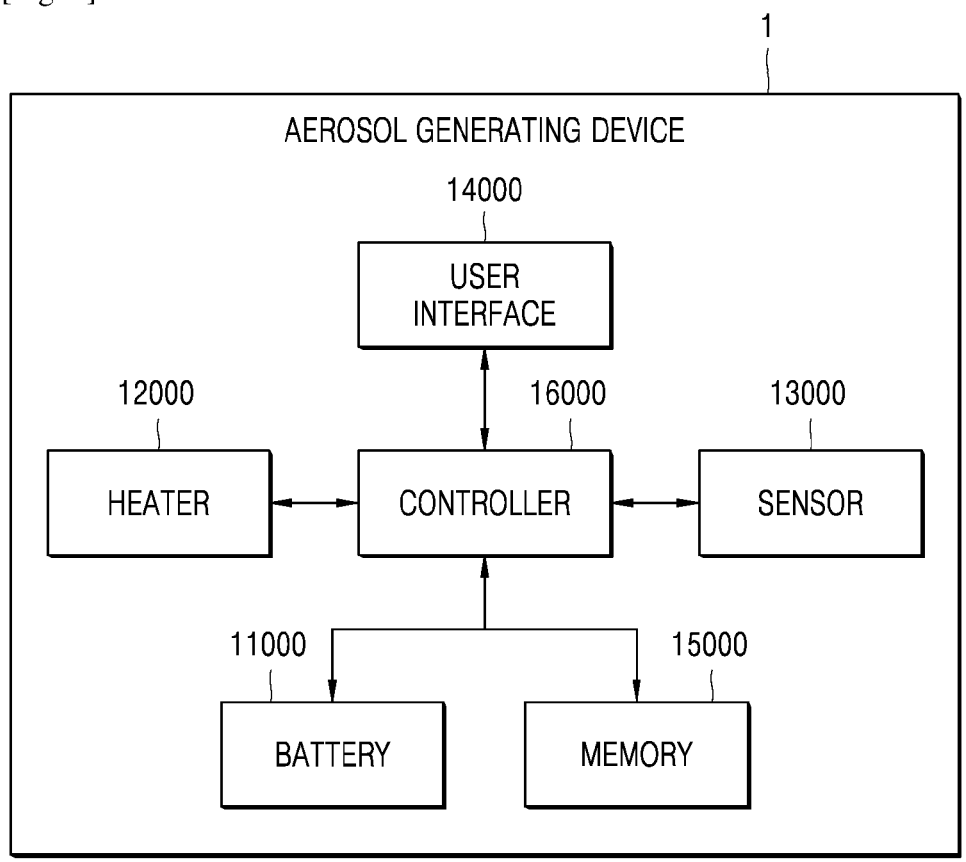

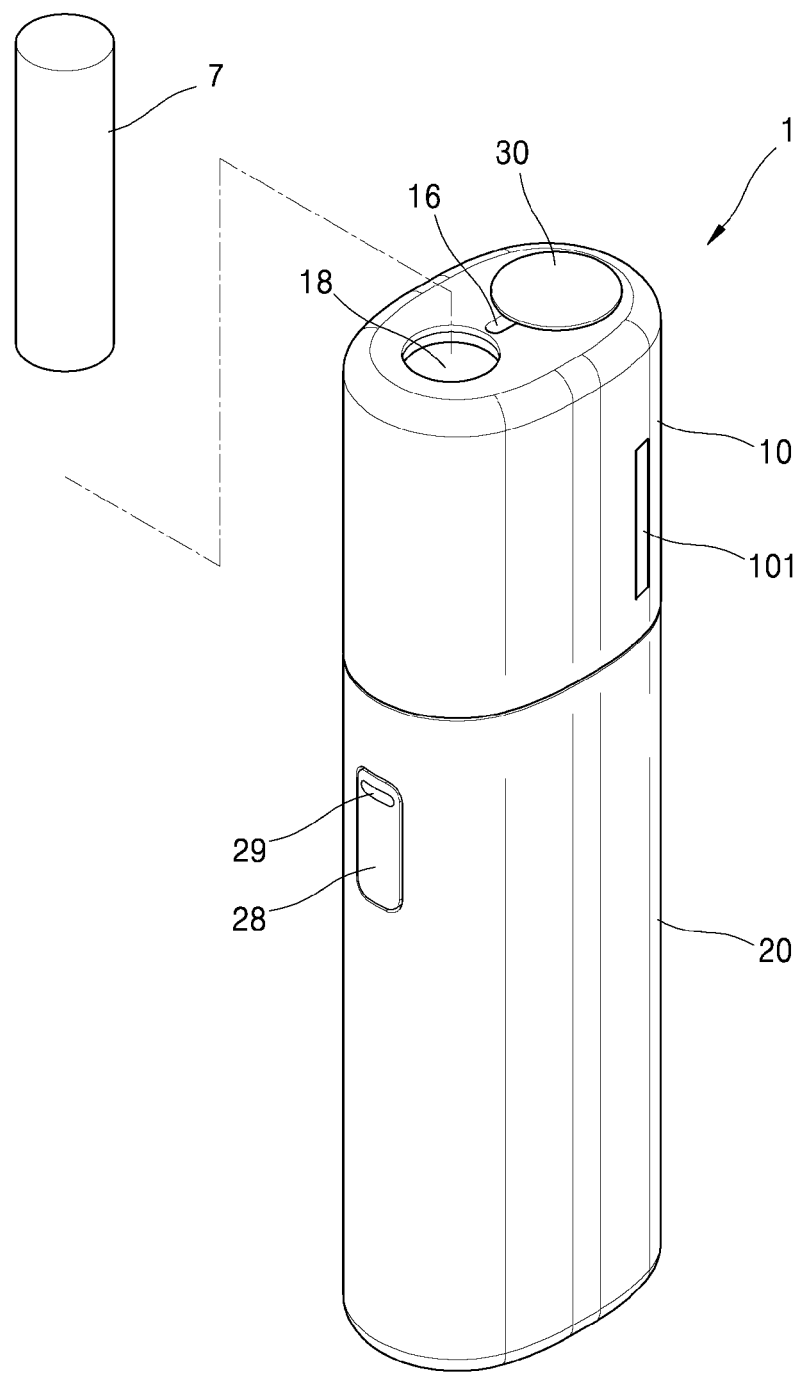

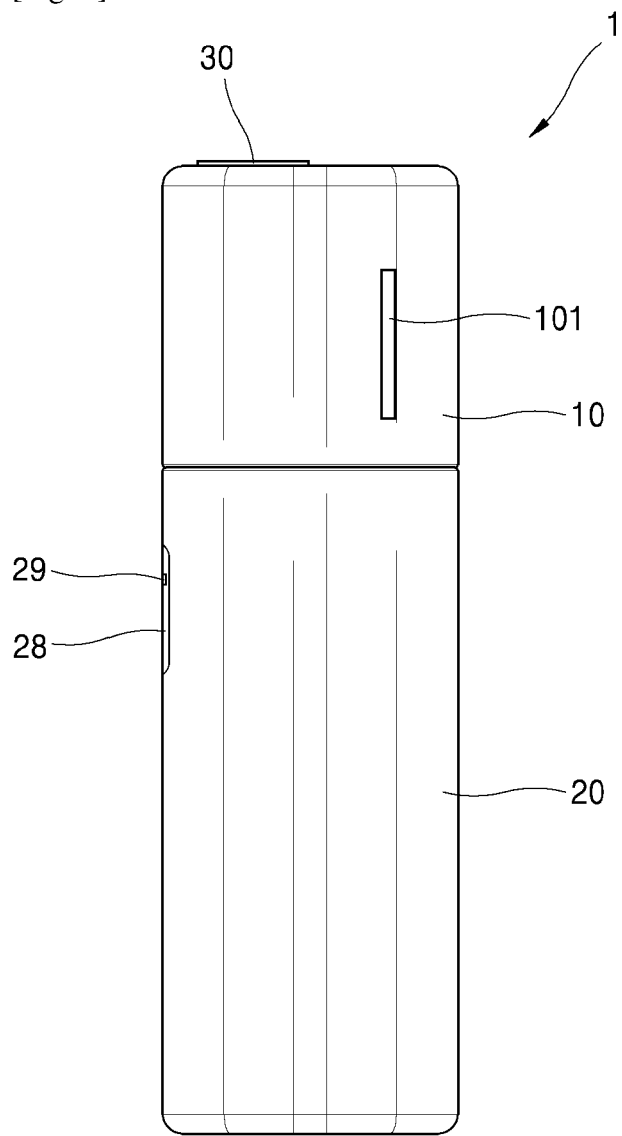
[Fig. 3]

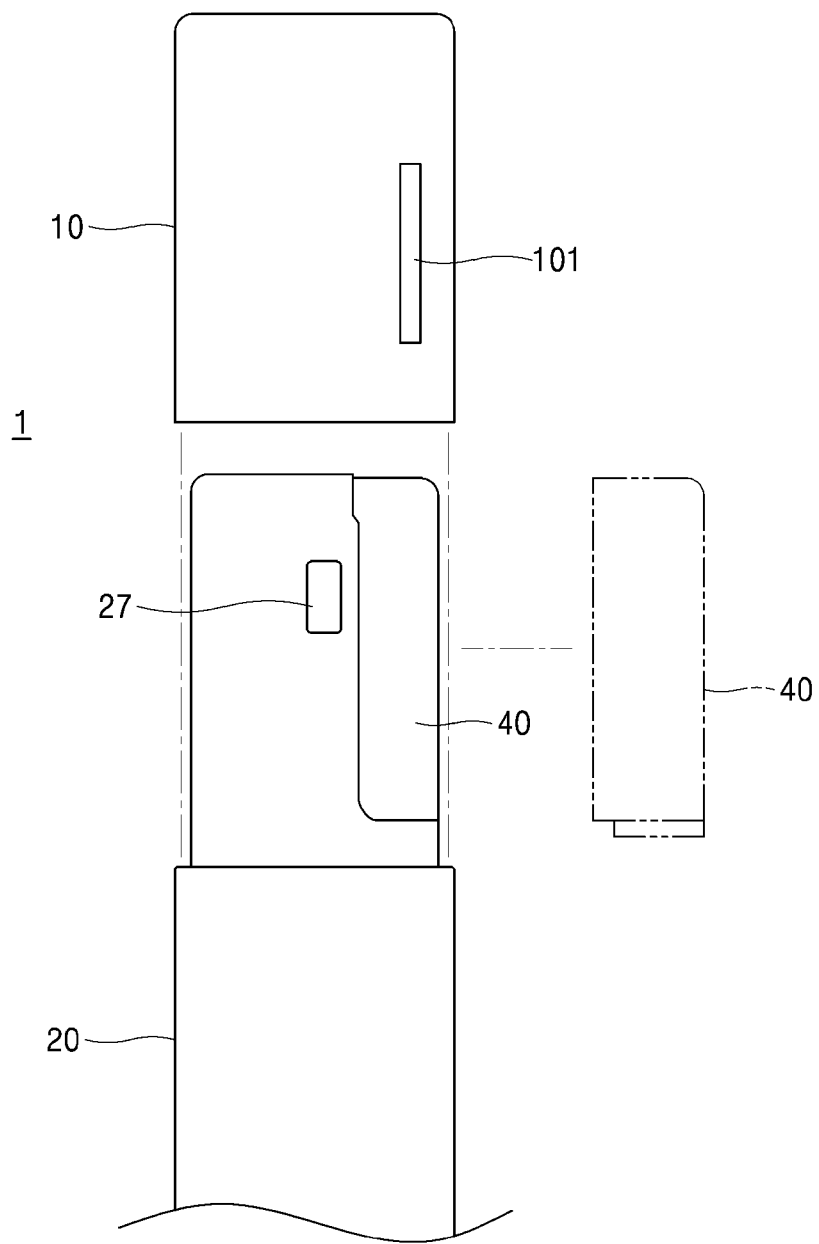
[Fig. 4]

[Fig. 5]
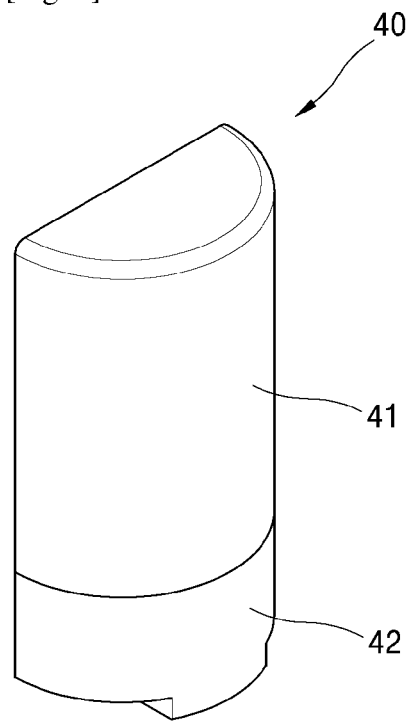
[Fig. 6A]
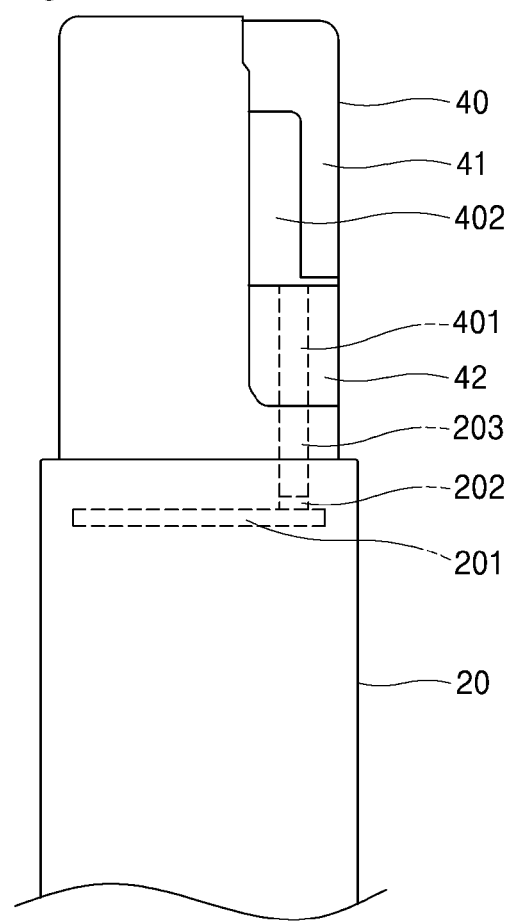

[Fig. 6B]
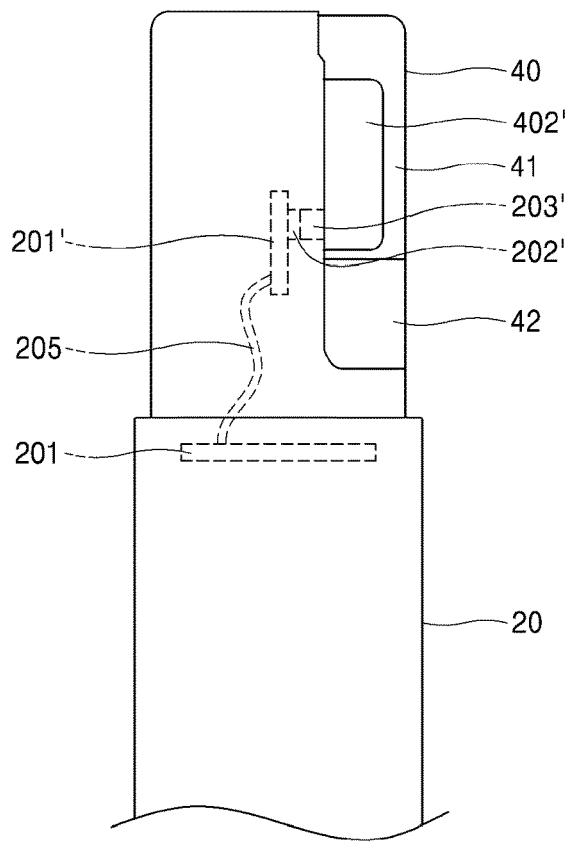
[Fig. 6C]
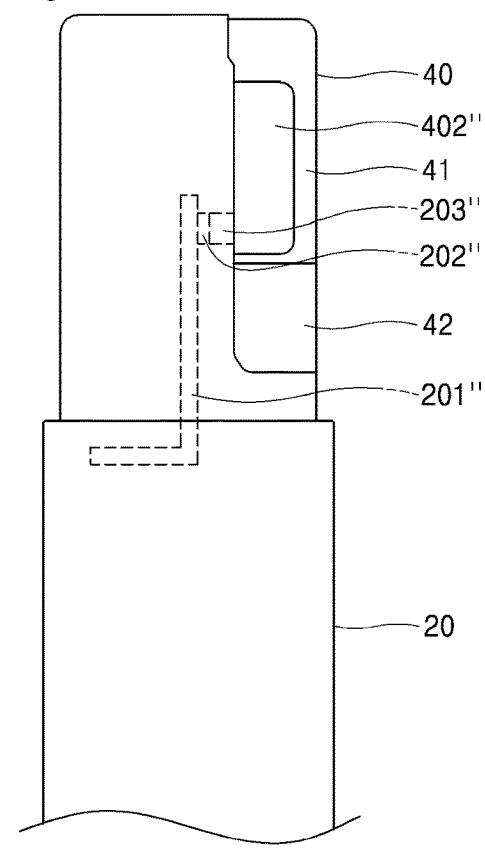

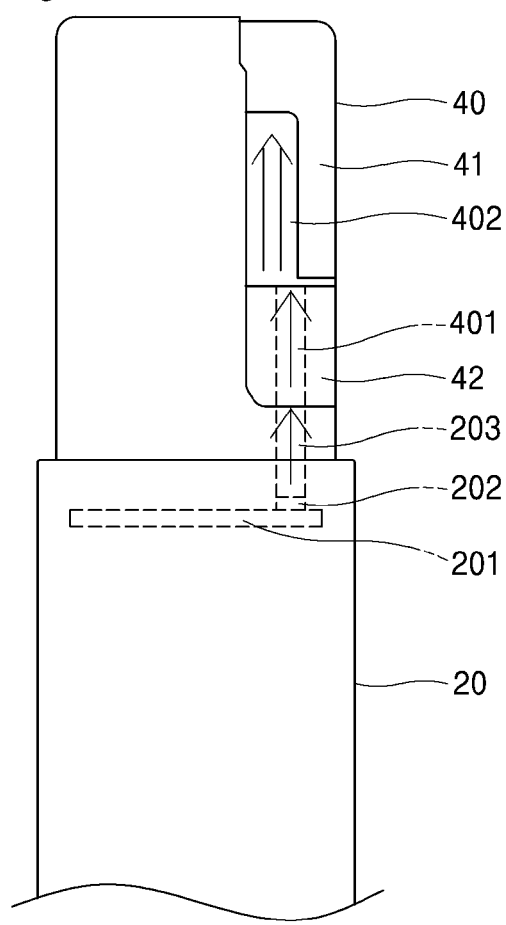
[Fig. 7]

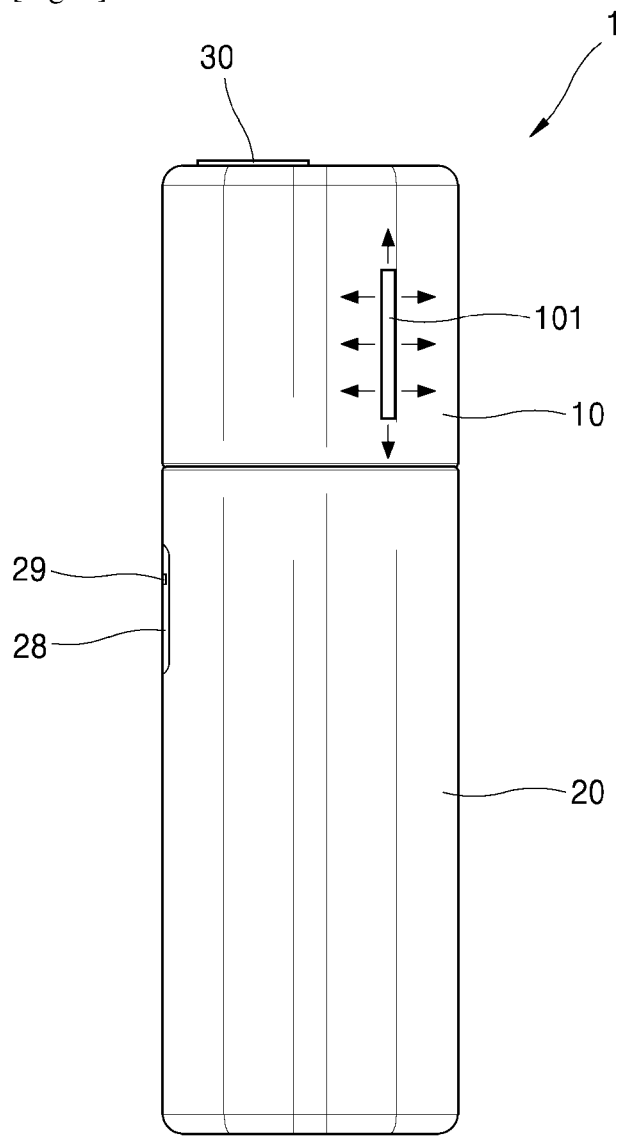
[Fig. 8]

[Fig. 9]
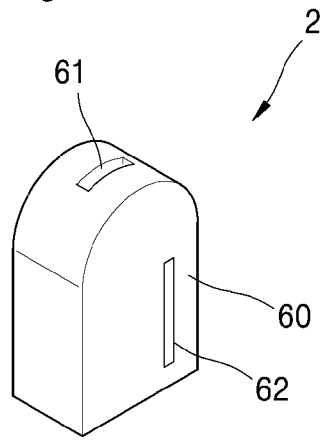
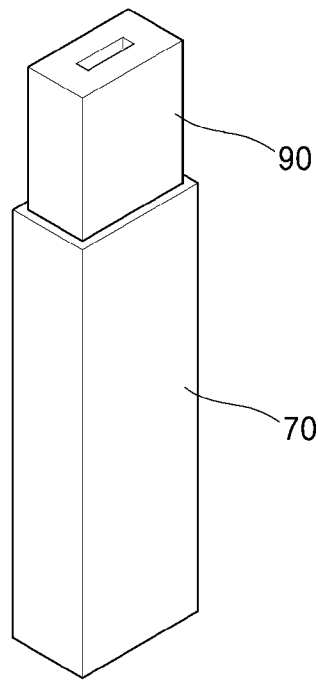

AEROSOL GENERATING DEVICE AND METHOD FOR SHOWING THE REMAINING AMOUNT OF LIQUID COMPOSITION USING LIGHT SOURCE

CROSS REFERENCE TO RELATED APPLICATIONS

This application is a National Stage of International Application No. PCT/KR2020/013574 filed Oct. 6, 2020, claiming priority based on Korean Patent Application No. 10-2019-0126291 filed Oct. 11, 2019.

TECHNICAL FIELD

The present disclosure relates to an aerosol generating device that generates an aerosol by heating an aerosol generating material.

BACKGROUND ART

Recently, demand for alternative methods to overcome the shortcomings of general cigarettes has increased. For example, there is growing demand for a heating-type aerosol generating device that generates an aerosol by heating an aerosol generating material in a cigarette instead of combusting a cigarette. Accordingly, research into a heating-type cigarette and a heating-type aerosol generating device is being actively conducted.

Furthermore, an aerosol generating device using a liquid composition needs to inform a user of the remaining amount of liquid composition.

DISCLOSURE OF INVENTION

Solution to Problem

The present disclosure provides an aerosol generating device that enables a user to easily check the remaining amount of liquid composition.

An aerosol generating device according to an aspect comprises a main body that comprises a battery and a controller, a cartridge which is coupled to the main body and comprises a liquid storage that contains liquid composition and an atomization portion that generates an aerosol by heating the liquid composition contained in the liquid storage, and a cover that forms an inner space by being coupled to the main body such that the cartridge is arranged in the inner space, wherein the main body further comprises a light source that emits light toward an inside of the liquid storage, and the cover comprises a window hole through which light emitted from the light source toward the inside of the liquid storage is transmitted out of the cover.

Advantageous Effects of Invention

A user may check the remaining amount of liquid composition contained in a cartridge through light emitted from a light source. In addition, the user may visually and intuitively check the remaining amount of liquid composition contained in the cartridge from light emitted from the light source.

Effects of present disclosure are not limited by content exemplified above, and more various effects are included in the present specification.

BRIEF DESCRIPTION OF DRAWINGS

FIG. 1 is a block diagram illustrating a hardware configuration of an aerosol generating device according to an embodiment;

FIGS. 2 to 4 illustrate an aerosol generating device according to an embodiment;

FIG. 5 illustrates a cartridge according to an embodiment;

FIGS. 6A to 6C schematically illustrate examples in which a light source is arranged in an aerosol generating device;

FIGS. 7 and 8 schematically illustrate an example of a path through which light travels; and FIG. 9 illustrates an aerosol generating device according to an embodiment.

BEST MODE FOR CARRYING OUT THE INVENTION

An aerosol generating device according to an aspect comprises a main body that comprises a battery and a controller, a cartridge which is coupled to the main body and comprises a liquid storage that contains liquid composition and an atomization portion that generates an aerosol by heating the liquid composition contained in the liquid storage, and a cover that forms an inner space by being coupled to the main body so that the cartridge is arranged in the inner space, wherein the main body further comprises a light source that emits light toward an inside of the liquid storage, and the cover comprises a window hole through which light emitted from the light source toward the inside of the liquid storage is transmitted to an outside of the cover.

The aerosol generating device further comprise a sensor that senses the remaining amount of liquid composition contained in the liquid storage, and the controller controls the light source based on the remaining amount of the liquid composition sensed by the sensor.

In the aerosol generating device, the controller changes a color of light emitted from the light source according to the remaining amount of the liquid composition sensed by the sensor.

In the aerosol generating device, the light source is arranged inside the main body, and the main body further comprises a first light guide portion that guides light emitted from the light source to the cartridge.

In the aerosol generating device, an exit surface of the first light guide portion faces the liquid storage.

In the aerosol generating device, the liquid storage includes a diffusion sheet arranged at a position corresponding to the exit surface of the first light guide portion so that light emitted from the first light guide portion is diffused along the diffusion sheet.

In the aerosol generating device, the atomization portion further comprises a second light guide portion that guides light emitted from the exit surface of the first light guide portion to the liquid storage by passing through the atomization portion.

In the aerosol generating device, an incident surface of the second light guide portion faces an exit surface of the first light guide portion, and an exit surface of the second light guide portion faces the liquid storage.

In the aerosol generating device, the liquid storage comprises the diffusion sheet arranged at a position corresponding to an exit surface of the second light guide portion so that light emitted from the second light guide portion is diffused along a diffusion sheet.

In the aerosol generating device, the light source is arranged in a longitudinal direction of the aerosol generating device with respect to the cartridge.

In the aerosol generating device, the light source is arranged in a direction crossing a longitudinal direction of the aerosol generating device with respect to the cartridge.

In the aerosol generating device, the controller comprises a circuit board, and the light source is mounted on the circuit board.

In the aerosol generating device, the circuit board is a flexible circuit board.

In the aerosol generating device, the cover further comprises a cigarette insertion hole.

In the aerosol generating device, the cover is a mouthpiece.

In the aerosol generating device, the cover comprises a plurality of windows holes, and any two of the plurality of windows face each other with an inner space therebetween.

Mode for the Invention

With respect to the terms used to describe the various embodiments, general terms which are currently and widely used are selected in consideration of functions of structural elements in the various embodiments of the present disclosure. However, meanings of the terms can be changed according to intention, a judicial precedence, the appearance of new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It will be understood that when an element or layer is referred to as being "over," "above," "on," "connected to" or "coupled to" another element or layer, it can be directly over, above, on, connected or coupled to the other element or layer or intervening elements or layers may be present. In contrast, when an element is referred to as being "directly over," "directly above," "directly on," "directly connected to" or "directly coupled to" another element or layer, there are no intervening elements or layers present. Like numerals refer to like elements throughout.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the embodiments set forth herein.

Hereinafter, embodiments of the present disclosure will be described in detail with reference to the drawings.

FIG. 1 is a block diagram illustrating hardware components of the aerosol generating device according to an embodiment.

An aerosol generating device 1 may comprise a battery 11000, a heater 12000, a sensor 13000, a user interface 14000, a memory 15000, and a controller 16000 as a hardware configuration. The hardware configuration elements included in the aerosol generating device 1 may be divided to be arranged in a main body and a cartridge.

The battery 11000 supplies electric power to be used for the aerosol generating device 1 to operate. In other words, the battery 11000 may supply power such that the heater 12000 may be heated. In addition, the battery 11000 may supply power required for operation of other hardware components included in the aerosol generating device 1, that is, the sensor 13000, the user interface 14000, the memory 15000, and the controller 16000. The battery 11000 may be a rechargeable battery or a disposable battery. For example, the battery 11000 may be a lithium polymer (LiPoly) battery, but is not limited thereto.

The heater 12000 receives power from the battery 11000 under the control of the controller 16000. The heater 12000 may receive power from the battery 11000 and heat a cigarette inserted into the aerosol generating device 1, or heat the cartridge mounted on the aerosol generating device 1.

The heater 12000 may be located in the main body of the aerosol generating device 1. Alternatively, the heater 12000 may be located in the cartridge. When the heater 12000 is located in the cartridge, the heater 12000 may be supplied with power from the battery 11000 located in at least one of the main body and the cartridge.

The heater 12000 may be formed of any suitable electrically resistive material. For example, the suitable electrically resistive material may be a metal or a metal alloy including titanium, zirconium, tantalum, platinum, nickel, cobalt, chromium, hafnium, niobium, molybdenum, tungsten, tin, gallium, manganese, iron, copper, stainless steel, or nichrome, but is not limited thereto. In addition, the heater 12000 may be implemented by a metal wire, a metal plate on which an electrically conductive track is arranged, or a ceramic heating element, but is not limited thereto.

In an embodiment, the heater 12000 may be a component included in the cartridge. The cartridge may comprise the heater 12000, the liquid delivery element, and the liquid storage. The aerosol generating material accommodated in the liquid storage may be moved to the liquid delivery element, and the heater 12000 may heat the aerosol generating material absorbed by the liquid delivery element, thereby generating aerosol. For example, the heater 12000 may comprise a material such as Nichrome and may be wound around or arranged adjacent to the liquid delivery element.

In another embodiment, the heater 12000 may heat the cigarette inserted into the accommodation space of the aerosol generating device 1. As the cigarette is accommodated in the accommodation space of the aerosol generating device 1, the heater 12000 may be located inside and/or outside the cigarette. Accordingly, the heater 12000 may generate aerosol by heating the aerosol generating material in the cigarette.

Meanwhile, the heater 12000 may comprise an induction heater. The heater 12000 may comprise an electrically conductive coil for heating a cigarette or the cartridge in an induction heating method, and the cigarette or the cartridge may comprise a susceptor winch may be heated by the induction heater.

The aerosol generating device 1 may comprise at least one sensor 13000. A result sensed by the at least one sensor 13000 is transmitted to the controller 16000, and the controller 16000 may control the aerosol generating device 1 to perform various functions such as controlling the operation of the heater, restricting smoking, determining whether a cigarette (or a cartridge) is inserted, and displaying a notification.

For example, the at least one sensor 13000 may comprise a puff detecting sensor. The puff detecting sensor may detect a user's puff based on any one of a temperature change, a flow change, a voltage change, and a pressure change.

In addition, the at least one sensor 13000 may comprise a temperature sensor. The temperature sensor may detect a temperature at which the heater 12000 (or an aerosol generating material) is heated. The aerosol generating device 1 may comprise a separate temperature sensor for sensing a temperature of the heater 12000, or the heater 12000 itself may serve as a temperature sensor instead of including a separate temperature sensor. Alternatively, a separate temperature sensor may be further included in the aerosol generating device 1 while the heater 12000 serves as a temperature sensor.

In addition, the at least one sensor 13000 may comprise a remaining amount sensor for measuring the remaining amount of liquid composition contained in the cartridge. For example, the remaining amount sensor may comprise a water level sensor for measuring a water level by detecting flow of electricity when an aerosol generating material, which is a conductive liquid, comes into contact with an electrode, an inductive sensor that uses a property that inductance changes according to a gap, an infrared sensor for measuring a remaining amount based on temperature, a capacitance sensor for measuring the remaining amount based on a change in capacitance, and so on.

The user interface 14000 may provide the user with information about the state of the aerosol generating device 1. The user interface 14000 may comprise various interfacing devices, such as a display or a light emitter for outputting visual information, a motor for outputting haptic information, a speaker for outputting sound information, input/output (I/O) interfacing devices (for example, a button or a touch screen) for receiving information input from the user or outputting information to the user, terminals for performing data communication or receiving charging power, and communication interfacing modules for performing wireless communication (for example, Wi-Fi, Wi-Fi direct, Bluetooth, near-field communication (NFC), etc.) with external devices.

However, the aerosol generating device 1 may be implemented by selecting only some of the above-described various interfacing devices.

The memory 15000 may be a hardware component configured to store various pieces of data processed in the aerosol generating device 1, and the memory 15000 may store data processed or to be processed by the controller 16000. The memory 15000 may comprise various types of memories, such as random access memory, such as dynamic random access memory (DRAM), static random access memory (SRAM), etc., read-only memory (ROM), electrically erasable programmable read-only memory (EPROM), etc.

The memory 15000 may store an operation time of the aerosol generating device 1, the maximum number of puffs, the current number of puffs, at least one temperature profile, data on a user's smoking pattern, etc.

The controller 16000 is a hardware component configured to control general operations of the aerosol generating device 1. The controller 16000 may comprise at least one processor. A processor can be implemented as an array of a plurality of logic gates or can be implemented as a combination of a general purpose microprocessor and a memory in which a program executable in the microprocessor is stored. It will be understood by one of ordinary skill in the art that the processor can be implemented in other forms of hardware.

The controller 16000 analyzes a result of the sensing by at least one sensor 13000, and controls processes that are to be performed subsequently.

The controller 16000 may control power supplied to the heater 12000 so that the operation of the heater 12000 is started or terminated, based on the result of the sensing by the at least one sensor 13000. In addition, based on the result of the sensing by the at least one sensor 13000, the controller 16000 may control the amount of power supplied to the heater 12000 and the time at which the power is supplied, so that the heater 12000 is heated to a predetermined temperature or maintained at an appropriate temperature.

In an embodiment, the controller 16000 may set a mode of the heater 12000 to a pre-heating mode to start the operation of the heater 12000 after receiving a user input to the aerosol generating device 1. In addition, the controller 16000 may switch the mode of the heater 12000 from the pre-heating mode to an operation mode after detecting a user's puff by using the puff detecting sensor. In addition, the controller 16000 may stop supplying power to the heater 12000 when the number of puffs reaches a preset number after counting the number of puffs by using the puff detecting sensor.

The controller 16000 may control the user interface 14000 based on the result of the sensing by the at least one sensor 13000. For example, when the number of puffs reaches the preset number after counting the number of puffs by using the puff detecting sensor, the controller 16000 may notify the user by using at least one of a light emitter, a motor or a speaker that the aerosol generating device 1 will soon be terminated.

The controller 16000 may control a light emission form of a light source based on a result sensed by the remaining amount sensor. For example, the controller 16000 may detect the remaining amount of liquid composition in a cartridge by using the remaining amount sensor, and then control the light emission mode of the light source to inform a user of the remaining amount of the liquid composition. For example, the controller 16000 may detect the remaining amount of the liquid composition in the cartridge by using the remaining amount sensor, and then change a light emission color of the light source according to the detected remaining amount of the liquid composition.

Although not illustrated in FIG. 1, an aerosol generating system may be configured by the aerosol generating device 1 and a separate cradle. For example, the cradle may be used to charge the battery 11000 of the aerosol generating device 1. For example, the aerosol generating device 1 may be supplied with power from a battery of the cradle to charge the battery 11000 of the aerosol generating device 1 while being accommodated in an accommodation space of the cradle.

FIGS. 2 to 4 illustrate an aerosol generating device according to an embodiment.

Referring to FIGS. 2 to 4, the aerosol generating device 1 may comprise a main body 20, a cartridge 40, and a cover 10.

The cover 10 may be coupled to one end of the main body 20 so that both the main body 20 and the cover 10 form an appearance of the aerosol generating device 1.

The cover 10 may be made of a plastic material that does not deliver heat well, or a metal material having a surface coated with a heat shielding material. The cover 10 may be made by using, for example, an injection molding method, a 3D printing method, or a method of assembling a small component formed by injection molding.

A maintenance device (not illustrated) may be installed between the main body 20 and the cover 10 to maintain a coupling state of the main body 20 and the cover 10. The maintenance device may comprise, for example, a protrusion and a groove. The coupling state of the cover 10 and the main body 20 may be maintained by maintaining a state in which the protrusion is inserted into the groove, and a structure in which the protrusion is released from the groove as the protrusion is moved by an operation button that may be pressed by a user may be used.

In addition, the maintenance device may comprise, for example, a magnet and a metal member that sticks to the magnet. When the magnet is used for the maintenance device, the magnet may be installed in one of the main body 20 and the cover 10, a metal member sticking to the magnet may be installed in the other, or the magnet may also be installed in both the main body 20 and the cover 10.

A cap 30 may be installed on an upper surface of the cover 10 so as to slidably move. A rail 16 extending in a slide movement direction of the cap 30 and a cigarette insertion hole 18 into which a cigarette 7 is inserted may be installed on an upper surface of the cover 10. The rail 16 may be opened to connect the outside to the inside of the cover 10.

When the cap 30 moves along the rail 16 formed on the upper surface of the cover 10 and the cigarette insertion hole 18 is exposed to the outside, the cigarette 7 may be inserted into the cigarette insertion hole 18.

As the cap 30 slides along the upper surface of the cover 10, various preparation operations may be performed in connection with an operation of opening the cigarette insertion hole 18 For example, at the moment when the cigarette insertion hole 18 is opened by the cap 30, a change in the operation mode of the aerosol generating device 1, preliminarily heating operations of internal heaters, a light emission operation of a light source, an operation of changing a light emission mode of the light source, an operation of recognizing a user, or so on may be performed.

The cigarette 7 may be similar to a general combustion-type cigarette. For example, the cigarette 7 may be divided into a first portion including an aerosol generating material and a second portion including a filter and so on. Alternatively, the second portion of the cigarette 7 may also comprise the aerosol generating material. For example, granules or an aerosol generating material made in the form of a capsule may be inserted into the second portion.

All the first portion is inserted into the cigarette insertion hole 18, and the second portion may be exposed to the outside. Alternatively, only a part of the first portion may also be inserted into the inside of the aerosol generating device 1, or all the first portion and a part of the second portion may be inserted thereinto. A user may inhale an aerosol while holding the second portion by the mouth.

The cartridge 40 may be arranged in an inner space formed coupling the main body 20 to the cover 10.

The cartridge 40 may be detachably attached to one end of the main body 20. For example, when a user presses a button 28, a fastening protrusion that is insertable into the cartridge 40 slides along a guide hole formed in the main body 20 in a vertical direction, and thus, the main body 20 and the cartridge 40 may be fastened to each other or separated from each other.

FIG. 4 illustrates that the cartridge 40 is installed in the main body 20 by approaching from a side of the main body 20, but embodiments are not limited thereto. For example, the cartridge 40 may also be installed in the main body 20 by approaching in a vertical direction from an upper side of the main body 20 like the cover 10.

The cartridge 40 may generate an aerosol by heating a liquid composition, and the generated aerosol may pass through the cigarette 7 to be delivered to a user. In other words, the aerosol generated by the cartridge 40 may move along an airflow path of the aerosol generating device 1, and the airflow path may be composed such that the aerosol generated by the cartridge 40 may pass through the cigarette to be delivered to the user.

The cover 10 may comprise a window hole 101. For example, the cover 10 may comprise two window holes 101 respectively arranged on opposite surfaces such as a front surface and a rear surface.

The window hole 101 may be arranged at a position corresponding to the cartridge 40. Preferably, the window hole 101 may face a liquid storage of the cartridge 40.

The window hole 101 may be narrowly elongated. A transparent window including a material having at least a part which is transparent may be arranged in the window hole 101. The transparent window may be made of a material such as plastic or glass.

The main body 20 may comprise a light source. Light emitted from a light source may be applied toward a liquid storage of the cartridge 40 and may be delivered to the user through the window hole 101.

Furthermore, the button 28 that may be operated by a user and a lamp 29 for displaying an internal operation state of the aerosol generating device 1 by selecting and emitting one of several colors previously determined may be installed on the outside of the main body 20 of the aerosol generating device 1. The lamp 29 may comprise a light emitting diode (LED).

The controller 16000 illustrated in FIG. 1 may operate the lamp 29 to emit light to display a "normal operation state" based on conditions such as a normal operation of a heater and/or a state of sufficient remaining capacity of a battery.

When a user performs an operation of pressing the button 28, the lamp 29 may emit light. The user may cheek the remaining amount of electric charge of the battery from a light emission color of the lamp 29. For example, the lamp 29 may emit green light when the amount of electricity charged by the battery is sufficient, and the lamp 29 may emit red light when the amount of electricity charged by the battery is insufficient.

Different pre-set operations may be performed according to a length of time that a user presses the button 28. For example, when the user presses the button 28 for a predetermined first pressing time, a reset (i.e., initialization of settings) operation of the aerosol generating device 1 may be performed. In addition, when the user presses the button 28 for a predetermined second pressing time, a preliminary heating operation of the aerosol generating device 1 may be performed.

In addition, when the user presses the button 28, a light source may emit light. For example, when the user performs an operation of pressing the button 28 once for a short time, an operation of pressing the button 28 twice in succession, an operation of pressing the button 28 for a predetermined period, and so on, the light source may emit light. The light source may emit light while the button 28 is pressed or may emit light for a predetermined period of time according to an input of the user pressing the button 28. The light emitted from a light source may be delivered to the user through the window hole 101.

The controller may control the light source to emit light bused on the remaining amount of liquid composition sensed by a sensor. For example, the controller may control the light source to change a color of light emitted from the light source according to the remaining amount of the liquid composition. A user may check the remaining amount of liquid composition from a color of light emitted through the window hole 101. As another example, the controller may control the light source to change properties of light such as intensity, blinking frequency, etc. according to the remaining amount of the liquid composition.

FIG. 5 illustrates the cartridge according to the embodiment.

The cartridge 40 may comprise a liquid storage 41 for containing liquid composition and an atomization portion 42 that converts an aerosol generating material in the liquid storage 41 into an aerosol.

For example, the liquid storage 41 may directly contain an aerosol generating material. Alternatively, the liquid storage 41 may include an element that contains an aerosol generating material such as sponge, cotton, cloth, or a porous ceramic structure.

The aerosol generating material may comprise liquid composition. For example, the liquid composition may be a liquid including a tobacco-containing material including volatile tobacco flavor ingredients or may be a liquid including a non-tobacco material.

The liquid composition may comprise, for example, water, solvent, ethanol, plant extract, perfume, flavoring agent, any one ingredient of a vitamin mixture, or a mixture thereof. The perfume may include menthol, peppermint, spearmint oil, and various fruit flavoring ingredients and is not limited thereto. The flavoring agent may include ingredients that may provide various flavors or savors to a user. A vitamin mixture may be a mixture of at least one of vitamin A, vitamin B, vitamin C, and vitamin E and is not limited thereto. In addition, the liquid composition may contain an aerosol former such as glycerin and propylene glycol.

For example, the liquid composition may include a solution of glycerin and propylene glycol of a certain weight ratio to which nicotine salt is added. The liquid composition may contain two or more nicotine salts. Nicotine salt may be formed by adding suitable acid including organic acid or inorganic acid to nicotine. Nicotine is naturally generated nicotine or synthetic nicotine and may have a certain suitable weight concentration to the total solution weight of the liquid composition.

Acid for forming the nicotine salt may be appropriately selected considering a rate of absorption of nicotine in the blood, an operation temperature of an aerosol generating device, flavor or savor, degree of solution, and so on. For example, the acid for the formation of nicotine salts may be a single acid selected from the group consisting of benzoic acid, lactic acid, salicylic acid, lauric acid, sorbic acid, levulinic acid, pyruvic acid, formic acid, acetic acid, propionic acid, butyric acid, valeric acid, caproic acid, caprylic acid, capric acid, citric acid, myristic acid, palmitic acid, stearic acid, oleic acid, linoleic acid, linolenic acid, phenylacetic acid, tartaric acid, succinic acid, fumaric acid, gluconic acid, saccharic acid, malonic acid or malic acid, or a mixture of two or more acids selected from the group, but is not limited thereto.

The atomization portion 42 may comprise a liquid delivery element that absorbs a liquid composition and maintains the liquid composition in an optimal state for conversion into an aerosol, a heater that generates an aerosol by heating the liquid delivery element, and a frame that supports the liquid delivery element and the heater and forms an atomization chamber that is a space in which the aerosol is generated.

The liquid delivery element may include at least one of, for example, a cotton fiber, a ceramic fiber, a glass fiber, and porous ceramic.

The heater may include a metal material such as copper, nickel, or tungsten to heat the liquid composition delivered to the liquid delivery element by generating heat caused by electric resistance. The heater may be implemented by, for example, a metal wire, a metal plate, a ceramic heating element, or so on and may be implemented by a conductive filament, wound on the liquid delivery element, or arranged adjacent to the liquid delivery element, by using a material such as a nichrome wire.

The atomization portion may be implemented by a mesh-shaped heating element or a plate-shaped heating element that absorbs a liquid composition without using a separate liquid delivery element, maintains the liquid composition in an optimal state for conversion to an aerosol, and heats the liquid composition to generate an aerosol.

FIGS. 6A to 6C schematically illustrate examples in which a light source is arranged in an aerosol generating device.

The main body 20 may comprise the controller 16000 illustrated in FIG. 1. The controller may comprise a circuit board 201, a microcontroller mounted on the circuit board 201, and so on.

The main body 20 may comprise a light source 202. The light source 202 may comprise at least one light emitting element. The at least one light emitting element may comprise a light emitting diode (LED). The at least one light emitting element may comprise a full color light emitting diode capable of emitting light of various colors.

For example, as illustrated in FIG. 6A, the light source 202 may be mounted on the circuit board 201. By mounting the light source 202 on the circuit board 201 of the controller without mounting the light source 202 on another circuit board, an increase in manufacturing cost of the aerosol generating device due to addition of another circuit board may be prevented.

As another example, as illustrated in FIG. 6B, a light source 202' may be mounted on another circuit board 201' other than the circuit board 201 of the controller. The circuit board 201' may be connected to the circuit board 201 of the controller through an electric wire 205 to exchange power or data. Because the light source 202' is mounted on the circuit board 201' other than the circuit board 201 of the controller, the light source 202' may be freely arranged inside the main body 20 regardless of a position of the circuit board 201.

As another example, as illustrated in FIG. 6C, a light source 202" may be mounted on a flexible circuit board

201". FIG. 6C illustrates the flexible circuit board 201" bent at 90 degrees. The flexible circuit board 201" may be included in the controller. As the light source 202" is mounted on the flexible circuit board 201", a degree of a position where the light source 202" is placed is increased, and at same time, an increase in manufacturing cost of the aerosol generating device due to addition of another circuit board may be prevented.

The light source 202 may be arranged so that light emitted from the light source 202 travels toward the inside of the liquid storage 41.

As illustrated in FIG. 6A, the light source 202 may be arranged in a longitudinal direction of the aerosol generating device with respect to the cartridge 40. That is, the light source 202 may be arranged under the cartridge 40.

The main body 20 may comprise a first light guide portion 203 that guides light emitted from the light source 202 toward the cartridge 40. An incident surface of the first light guide portion 203 may face the light source 202, and an exit surface of the first light guide portion 203 may be arranged toward the cartridge 40.

When the light source 202 faces the cartridge 40, that is, when the light source 202 is arranged to be exposed to the outside of the main body 20, the main body 20 may not include the first light guide portion 203.

The atomization portion 42 of the cartridge 40 may comprise a second light guide portion 401 that guides light exiting the first light guide portion 203 to the liquid storage 41. An incident surface of the second light guide portion 401 may face an exit surface of the first light guide portion 203, and the exit surface of the second light guide portion 401 may face the liquid storage 41.

The second light guide portion 401 may be arranged to be separated from an atomization chamber of the atomization portion 42. As such, the second light guide portion 401 may be prevented from being thermally deformed due to a heater. In addition, the second light guide portion 401 may be supported by the frame of the atomization portion 42.

The second light guide portion 401 may be arranged to pass through the atomization portion 42. For example, the second light guide portion 401 may be arranged inside the atomization portion 42 to pass through the atomization portion 42. In an embodiment, the second light guide portion 401 may be arranged to pass through the atomization portion 42 while being in contact with the surface of the atomization portion 42.

The liquid storage 41 may comprise a diffusion sheet 402 arranged at a position corresponding to the exit surface of the second light guide portion 401. Light passing through the second light guide portion 401 may be diffused along the diffusion sheet 402. That is, the diffusion sheet 402 may convert the light emitted from the light source 202 into a surface light source having more uniform brightness.

The diffusion sheet 402 may be attached to a surface of the liquid storage 41. For example, the diffusion sheet 402 may be attached to the surface of the liquid storage 41 facing the exit surface of the second light guide portion 401. For example, the diffusion sheet 402 may be attached to a lower surface of the liquid storage 41. In addition, the diffusion sheet 402 may be attached to a side surface of the liquid storage 41. In addition, the diffusion sheet 402 may be attached to a portion of the side surface of the liquid storage 41, which faces the window hole 101 (illustrated in FIG. 2) of the cover.

The first light guide portion 203 and the second light guide portion 401 may be formed of glass, silicon, plastic, or so on so that light may easily pass therethrough. For example, the first light guide portion 203 and the second light guide portion 401 may comprise optical fibers such as glass fibers and plastic fibers.

When a part of the frame of the atomization portion 42 is transparent, the light passing through the first light guide portion 203 may pass through a transparent portion of the frame to reach the liquid storage 41. In this case, the atomization portion 42 may not comprise the second light guide portion 401.

Alternatively, as illustrated in FIGS. 6B and 6C, the light sources 202" and 202"? may be arranged in a direction crossing a longitudinal direction of the aerosol generating device with respect cartridge 40. That is, the light sources 202" and 202"? may be arranged in a lateral direction of the cartridge 40. In this case, the surfaces of the first light guide portions 203" and 203"? may be arranged toward the liquid storage 41. Because the light passing through the first light guide portions 203" and 203"? directly travels toward the liquid storage 41, the atomization portion 42 may not comprise the second light guide portion 401.

The liquid storage 41 may comprise diffusion sheets 402" and 402"? arranged at positions corresponding to exit surfaces of the first light guide portions 203" and 203"?. Light passing through the first light guide portions 203" and 203"? may be diffused along the diffusion sheets 402" and 402"?.

The diffusion sheets 402" and 402"? may be attached to a surface of the liquid storage 41. For example, the diffusion sheets 402" and 402"? may be attached to a surface of the liquid storage 41 facing the surfaces of the first light guide portions 203" and 203"?. For example, the diffusion sheets 402" and 402"? may be attached to a side surface of the liquid storage 41. In addition, the diffusion sheets 402" and 402"? may be attached to a portion of the side surface of the liquid storage 41, which faces the window hole of the cover.

When the light sources 202" and 202"? face the cartridge 40, that is, when the light sources 202" and 202"? are arranged to be to the outside of the main body 20, the main body 20 may not comprise the first light guide portions 203" and 203"?.

FIGS. 7 and 8 schematically illustrate examples of a path through which light travels.

FIG. 7 schematically illustrates an example of a path through which light emitted from the light source illustrated in FIG. 6A travels. The path through which the light travels is schematically illustrated in FIGS. 7 and 8 with arrows.

Referring to FIGS. 7 and 8, the controller 16000 illustrated in FIG. 1 may control the light source 202 to emit light. The controller may control the light source 202 to emit light at a predetermined time. For example, the controller may control the light source 202 to emit light during a period between puffs, when the number of puffs reach a certain number, or when a predetermined time elapses after smoking starts.

Alternatively, the controller may control the light source 202 to emit light according to an input signal. For example, the controller may control the light source 202 to emit light when a user presses the button 28. As another example, the controller may control the light source 202 to emit light when a user slides the cap 30.

Alternatively, the controller may control the light source 202 to emit light according to the remaining amount of liquid composition. Fix example, the controller may control the light source 202 to emit light when the remaining amount of the liquid composition sensed by a remaining amount sensor reaches a preset value.

The controller may control a light emission mode in which the light source 202 emits light. For example, the controller may change a color and intensity of light emitted from the light source 202. As another example, the controller may change a period and a cycle of the light source 202 emitting light.

The controller may change the color of the light emitted from the light source 202 according to the remaining amount of the liquid composition contained in the liquid storage 41. For example, the controller may change the color of the light emitted from the light source 202 according to a change in a value of the remaining amount of the liquid composition. As another example, the controller may change a color of light emitted from the light source 202 according to a change in the number of puffs with the remaining amount of liquid composition.

The controller may change the color of the light emitted from the light source 202 into three or more colors according to the remaining amount of the liquid composition contained in the liquid storage 41. The number of colors emitted from the light source 202 is not limited. The controller may change the color of the light source 202 according to the remaining amount of the liquid composition, and thus, a user may recognize easily and visually the remaining amount of the liquid composition.

The light emitted from the light source 202 may travel toward the cartridge 40 by passing through the first light guide portion 203. The light emitted from the exit surface of the first light guide portion 203 may travel toward the liquid storage 41 by passing through the second light guide portion 401. The light emitted from the exit surface of the second light guide portion 401 may be diffused by the diffusion sheet 402 of the liquid storage 41. The light diffused by the diffusion sheet 402 may be delivered to a user through the window hole 101. The user may visually recognize the light through the window hole 101 and may intuitively check the remaining amount of the liquid composition contained in the liquid storage 41 based on the light.

FIG. 9 illustrates an aerosol generating device according to an embodiment.

An aerosol generating device 2 may comprise a main body 70, a cartridge 90, and a cover 60. The aerosol generating device 2 may comprise a configuration and a function of the aerosol generating device described above. However, the aerosol generating device 2 may not comprise a configuration relating to a cigarette.

The cover 60 of the aerosol generating device 2 may function as a mouthpiece through which an aerosol generated from the cartridge 90 passes. The cover 60 comprises an opening 61, and an aerosol discharged through the opening 61 may be delivered to the mouth of a user.

In addition, the cover 60 may comprise a window hole 62. Light emitted from a light source installed in the main body 70 may be emitted to the outside through the cartridge 90 and the window hole 62. A user may check the remaining amount of liquid composition in the cartridge 90 from the light emitted through the window hole 62.

At least one of the components, elements, modules or units (collectively "components" in this paragraph) represented by a block in the drawings such as the controller 16000 in FIG. 1 may be embodied as various numbers of hardware, software and/or firmware structures that execute respective functions described above, according to an exemplary embodiment. For example, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Further, although a bus is not illustrated in the above block diagrams, communication between the components may be performed through the bus. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

Those skilled in the art relating to the present embodiments may understand that various changes in form and details may be made therein without departing from the scope of the characteristics described above. The disclosed methods should be considered in a descriptive sense only and not for purposes of limitation. The scope of the present disclosure is represented in the claims rather than the above description, and all differences within the scope equivalent thereto should be construed as being included in the present disclosure.

The invention claimed is:

1. An aerosol generating device for generating an aerosol, comprising:
   a main body comprising a battery and a controller;
   a cartridge coupled to the main body and comprising:
     a liquid storage that contains liquid composition; and
     an atomization portion configured to generate an aerosol by heating the liquid composition contained in the liquid storage;
   a cover configured to form an inner space by being coupled to the main body such that the cartridge is arranged in the inner space,
   wherein the main body further comprises a light source configured to emit light toward an inside of the liquid storage, and
   wherein the cover comprises a window hole through which light emitted from the light source toward the inside of the liquid storage is transmitted to an outside of the cover.

2. The aerosol generating device of claim 1, further comprising:
   a sensor configured to sense a remaining amount of the liquid composition contained in the liquid storage,
   wherein the controller controls the light source to light based on the remaining amount of the liquid composition sensed by the sensor.

3. The aerosol generating device of claim 2, wherein the controller changes a color of light emitted from the light source according to the remaining amount of the liquid composition sensed by the sensor.

4. The aerosol generating device of claim 1,
   wherein the light source is arranged inside the main body, and
   wherein the main body further comprises a first light guide portion that guides light emitted from the light source to the cartridge.

5. The aerosol generating device of claim 4, wherein an exit surface of the first light guide portion faces the liquid storage.

6. The aerosol generating device of claim 5, wherein the liquid storage comprises a diffusion sheet arranged at a position corresponding to the exit surface of the first light guide portion such that light emitted from the first light guide portion is diffused along the diffusion sheet.

7. The aerosol generating device of claim 4, wherein the atomization portion further comprises a second light guide portion that guides light emitted from the exit surface of the first light guide portion to the liquid storage by passing through the atomization portion.

8. The aerosol generating device of claim 7, wherein an incident surface of the second light guide portion faces the exit surface of the first light guide portion, and an exit surface of the second light guide portion faces the liquid storage.

9. The aerosol generating device of claim 7, wherein the liquid storage comprises a diffusion sheet arranged at a position corresponding to an exit surface of the second light guide portion such that light emitted from the second light guide portion is diffused along the diffusion sheet.

10. The aerosol generating device of claim 1, wherein the light source is arranged in a longitudinal direction of the aerosol generating device with respect to the cartridge.

11. The aerosol generating device of claim 1, wherein the light source is arranged in a direction crossing a longitudinal direction of the aerosol generating device with respect to the cartridge.

12. The aerosol generating device of claim 1,
wherein the controller comprises a circuit board, and
wherein the light source is mounted on the circuit board.

13. The aerosol generating device of claim 12, wherein the circuit board is a flexible circuit board.

14. The aerosol generating device of claim 1, wherein the cover further comprises a cigarette insertion hole.

15. The aerosol generating device of claim 1, wherein the cover is a mouthpiece.

* * * * *